United States Patent
Mathur et al.

(10) Patent No.: US 8,054,464 B2
(45) Date of Patent: Nov. 8, 2011

(54) POLARIZATION SWITCHING LIDAR DEVICE AND METHOD

(75) Inventors: Savyasachee Liptarag Mathur, Silver Spring, MD (US); Yunhui Zheng, Crofton, MD (US); Edward Lee Leventhal, Brookeville, MD (US)

(73) Assignee: Sigma Space Corp., Lanham, MD (US)

( * ) Notice: Subject to any disclaimer, the term of this patent is extended or adjusted under 35 U.S.C. 154(b) by 94 days.

(21) Appl. No.: 12/693,172

(22) Filed: Jan. 25, 2010

(65) Prior Publication Data
US 2011/0181881 A1    Jul. 28, 2011

(51) Int. Cl.
*G01N 21/00* (2006.01)
(52) U.S. Cl. .................. 356/342; 356/337
(58) Field of Classification Search .......... 356/335–343; 250/334, 332, 330; 342/33, 23, 188, 5
See application file for complete search history.

(56) References Cited

U.S. PATENT DOCUMENTS
5,721,632 A * 2/1998 Billmers et al. .............. 359/252
* cited by examiner

*Primary Examiner* — Tri T Ton
(74) *Attorney, Agent, or Firm* — Miodrag Cekic

(57) ABSTRACT

A polarization switching lidar device is arranged for remote detection and characterization of airborne aggregations of particulates. It includes a pulsed laser, a mirror, a polarizing beam splitter, an actively controlled retarder arranged to be controllably alternated between a zero retardation state and a quarter-wave retardation state such that the transmitted portion of the exiting laser light beam is linearly polarized in a predetermined direction when the actively controlled retarder is in the zero retardation state, while being circularly polarized in a predetermined rotational sense when the actively controlled retarder is in the quarter-wave retardation state. A directable telescoping assembly is arranged to collect photons backscattered by the airborne aggregations of particulates and to redirect the collected portion of depolarized backscattered photons onto the polarizing beam splitter. A photodetector is arranged to generate at least one electronic signal proportional to the collected portion of depolarized backscattered photons.

30 Claims, 5 Drawing Sheets

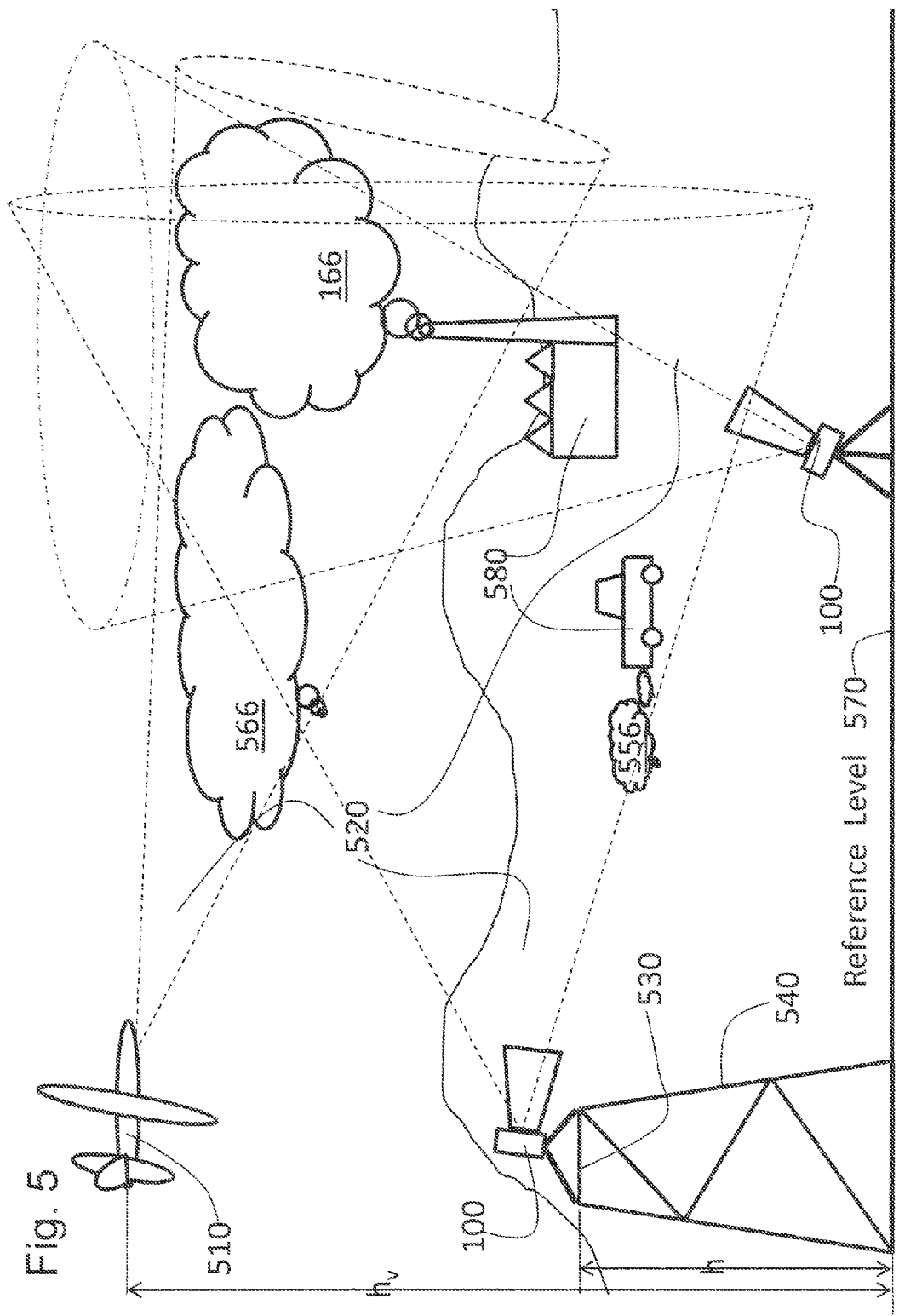

POLARIZATION SWITCHING LIDAR DEVICE AND METHOD

FIELD OF THE INVENTION

The invention relates generally to fixed and scanning lidar systems, and in particular to a polarization switching lidar device for remote detection and characterization of airborne aggregation of particulate.

BACKGROUND OF THE INVENTION

Many diverse applications may benefit from an effective remote detection and characterization of airborne aggregations of particulates. For example, climate change studies have shown that cloud effects and aerosol-cloud interactions (i.e. aerosol indirect effects) are among the largest uncertainties in simulations of climate change. Elastic backscatter lidars are highly sensitive instruments capable of providing profiles of clouds, aerosols, and other particulates aggregation structures within the atmosphere. An addition of polarization-sensitive detection provides information pertaining to the phase of cloud particulates and to the type of aerosol particulates. The U.S. DOE Atmospheric Radiation Measurements (ARM) Program has deployed eye-safe lidars for semi-autonomous operation at each of its climate research facilities for over a decade. Recently, polarization-sensitive lidar systems have been deployed by ARM through straightforward modifications of pre-existing designs and equipment.

Remote detection and stand-off characterization of chemical/biological agents may be a decisive factor in early warning chemical/biological systems allowing for improved survivability of personnel in the battlefield and/or other targeted or associated areas. One exemplary system incorporating a pulsed lidar operating using visible light is described by Lee, et al, "Micro Pulse lidar for Aerosol & Cloud Measurement", Advances in Atmospheric Remote Sensing with lidar, pp. 7-10, A. Ansmann, Ed., Springer Verlag, Berlin, 1997, while a near IR, is described, for example, by Condatore, et al, "U.S. Army Soldier and Biological Chemical Command Counter Proliferation Long Range—Biological Standoff Detection System (CP LR BSDS)", Proceedings of SPIE, Vol. 3707, 1999. the entire contents of which are incorporated herein by reference, have demonstrated the high sensitivity and long-range (up to 50 km) capability to detect aerosol clouds. Consequently, an aerosol lidar is a demonstrated technique for long-range detection and characterization of bio-warfare aerosols. Furthermore, similar lidar systems may be used for remote sensing and stand-off detection of air polluting aggregations of particulates generated by intentional commercial activities or accidentally released particulate aggregations.

The polarization switching lidar devices for remote detection and characterization of airborne aggregation of particulates in accordance with the present invention are essentially sensitive to the polarization relative to a predetermined plane of polarization. Therefore, any phase retardation that contributes to the same relative angle of polarization with respect to the predetermined plain of polarization cannot be resolved and are considered identical. More particularly, all phase retardation states having phase differences ("retardations") $\Delta\phi=n\pi$ radians ($n=0, \pm 1, \pm 2, \pm 3 \ldots$) are considered substantially equal and inclusively designated as a "zero retardation state", while all phase retardation states having phase differences ("retardations") $\Delta\phi=m\pi/2$ radians ($m=\pm 1, \pm 3, \pm 5 \ldots$) are considered substantially equal and inclusively designated as a "quarter-wave retardation state" for the purposes of the further recitations.

SUMMARY OF THE INVENTION

The present invention is directed to a polarization switching lidar device for remote detection and characterization of at least one airborne aggregation of particulates including a source of a polarized pulsed laser light beam; a direction controlling mirror arranged to reflect the polarized pulsed laser light beam and redirect the reflected polarized pulsed laser light beam; a polarizing beam splitter arranged to intersect the reflected polarized pulsed laser light beam and to redirect a portion of the reflected polarized pulsed laser light beam; an actively controlled retarder arranged to intersect the redirected portion of the reflected polarized pulsed laser light beam, and to be controllably alternated between a zero retardation state and a quarter-wave retardation state such that the transmitted portion of the polarized pulsed laser light beam exiting the actively controlled retarder is linearly polarized in a predetermined direction when the actively controlled retarder is in the zero retardation state, while the transmitted portion of the polarized pulsed laser light beam exiting the actively controlled retarder is circularly polarized in a predetermined rotational sense when the actively controlled retarder is in the quarter-wave retardation state; a directable (i.e. arranged to be manually or automatically specially oriented in at least one direction of interest in order to observe a predetermined sets of space angles) telescoping assembly arranged to intersect the transmitted portion of the polarized pulsed laser light beam exiting the actively controlled retarder and to controllably redirect the intersected polarized pulsed laser light beam into a predetermined space angle while collecting at least a portion of depolarized backscattered photons from the scanned polarized pulse laser light beam backscattered by the at least one airborne aggregations of particulates, and to redirect the collected portion of depolarized backscattered photons onto the polarizing beam splitter; an optical matcher arranged to collect a fraction of backscattered photons exiting the polarizing beam splitter and focus the collected fraction of depolarized backscattered photons onto a photodetector arranged to generate at least one electronic signal proportional to the collected portion of depolarized backscattered photons.

In addition, another apparatus embodying the present invention incorporates a polarization switching lidar device for remote detection and characterization of at least one airborne aggregation of particulates including a source of a polarized pulsed laser light beam; a first actively controlled retarder arranged to intersect the polarized pulsed laser light beam, to transmit a portion of the polarized pulsed laser light beam, and to be controllably alternated between a zero retardation state and a quarter-wave retardation state such that the transmitted portion of the polarized pulsed laser light beam exiting the first actively controlled retarder 150 is linearly polarized in a predetermined direction when the actively controlled retarder is in the zero retardation state, while the transmitted portion of the polarized pulsed laser light beam exiting the first actively controlled retarder is circularly polarized in a predetermined rotational sense when the first actively controlled retarder is in the quarter-wave retardation state; a first directable telescoping assembly arranged to intersect the transmitted portion of the polarized pulsed laser light beam exiting the first actively controlled retarder and to controllably redirect the intersected polarized pulsed laser light beam into a predetermined space angle; a second directable telescoping assembly arranged to collect at least a portion of backscattered photons from the scanned polarized pulse laser light beam backscattered by the at least one airborne aggregations of particulates, and to redirect the collected portion of backscattered photons along a detection optical path; a second actively controlled retarder arranged along the detection optical path to intersect the collected portion of backscattered photons, to transmit a fraction of the collected portion of backscattered photons, and to be controllably alternated between a zero retardation state and a quarter-wave retardation state such that the transmitted fraction of the collected portion of backscattered photons exiting the second actively controlled retarder is linearly polarized when the first actively controlled retarder is in the zero retardation state, while the transmitted fraction of the collected portion of backscattered photons exiting the second actively controlled retarder is linearly polarized in a direction perpendicular to the predetermined direction when the first actively controlled retarder is in the quarter-wave retardation state; a polarizer arranged to intersect the backscattered photons exiting the second actively controlled retarder and to selectively transmit only a part of the backscattered photons exiting the second actively controlled retarder which is linearly polarized in the direction perpendicular to the predetermined direction; an optical matcher arranged to collect the transmitted part of the backscattered photons exiting the polarizer and to focus the transmitted part of the backscattered photons exiting the polarizer onto a photodetector arranged to generate at least one electronic signal proportional to the collected part of the backscattered photons exiting the polarizer which is linearly polarized in the direction perpendicular to the predetermined direction.

Furthermore, a method embodying the present invention includes steps of generating a linearly polarized pulsed laser light beam having a predetermined direction of linear polarization; using at least one the actively controlled retarder, sequentially controllably switching a polarization state of the polarized pulsed laser light beam between a circularly polarized state polarized into a predetermined rotational sense, when the at least one actively controlled retarder is controllably switched into a quarter-wave retardation state, and into a linearly polarized state linearly polarized in a direction substantially equivalent to the predefined direction of linear polarization when the at least one actively controlled retarder is controllably switched into a zero retardation state such that a transmitted portion of polarized pulsed laser light beam exiting the at least one actively controlled retarder is linearly polarized in the predetermined polarization direction when the at least one actively controlled retarder is in the zero retardation state while the transmitted portion of polarized pulsed laser light beam exiting the at least one actively controlled retarder is circularly polarized having the predetermined rotational sense when the at least one actively controlled retarder is in the quarter-wave retardation state; scanning the transmitted portion of polarized pulsed laser light beam exiting the actively controlled retarder by at least one telescoping assembly arranged to intersect the transmitted portion of polarized pulsed laser light beam exiting the actively controlled retarder and controllably redirect the intersected polarized pulsed laser light beam into a predetermined space angle toward at least one airborne aggregation of particulates; backscattering the scanned transmitted portion of the polarized pulsed laser light beam sequentially polarized into the circularly polarized state having the predetermined rotational sense and into the linearly polarized state having the predetermined polarization direction so that a fraction of photons scatters back from at least one airborne aggregation of particulates such that the photons in circularly polarized state having the predetermined rotational sense acquire an opposite rotational sense of circular polarization, while at least a fraction of photons polarized in the predetermined linearly polarized state, when scattered back, acquires a linear polarization state polarized in an orthogonal direction relative to the predetermined direction of linear polarization; collecting photons from the predetermined space angle and redirecting the collected photons onto the actively controlled retarder by the at least one telescoping assembly; sequentially converting by the actively controlled retarder in the quarter-wave retardation state the collected backscattered photons having the circularly polarized state polarized in the opposite rotational sense relative to the rotational sense of the predetermined sense of circular polarization into the linearly polarized state having the polarization state polarized in an orthogonal direction relative to the predetermined direction of linear polarization, while transmitting the scattered back photons polarized in the linear polarization state having orthogonal direction of linear polarization relative to the predetermined direction of linear polarization when the actively controlled retarder in the zero retardation state, and redirecting the converted photons onto the polarizing beam splitter; selectively separating the converted photons collected sequentially onto the polarizing beam splitter by transmitting only the linearly polarized photons having orthogonal direction of linear polarization relative to the predetermined direction of linear polarization; optically matching the transmitted linearly polarized photons having orthogonal direction of linear polarization relative to the predetermined direction of linear polarization using an optical matcher arranged to collect at least a fraction of the transmitted linearly polarized photons having orthogonal direction of linear polarization relative to the predetermined direction of linear polarization and focus the transmitted linearly polarized photons having orthogonal direction of linear polarization relative to the predetermined direction of linear polarization onto a photodetector arranged to generate at least two electronic signals proportional to the transmitted linearly polarized photons having orthogonal direction of linear polarization relative to the predetermined direction of linear polarization; and separating at least one electrical signal generated during the quarter-wave retardation state of the from the at least two electrical signals from the at least another electrical signal generated during the zero retardation state of the actively controlled retarder and storing the separated signals into at least two dedicated memory sections.

DETAILED DESCRIPTION OF THE DRAWINGS

The above and other embodiments, features, and aspects of the present invention are considered in more detail in relation to the following description of embodiments shown in the accompanying drawings, in which:

FIG. 5 is an illustration of additional exemplary embodiments of the polarization switching lidar devices according to the present invention.

DETAILED DESCRIPTION OF THE INVENTION

The invention summarized above may be better understood by referring to the following description, which should be read in conjunction with the accompanying drawings. This description of an embodiment, set out below to enable one to build and use an implementation of the invention, is not intended to limit the invention, but to serve as a particular example thereof. Those skilled in the art should appreciate that they may readily use the conception and specific embodiments disclosed as a basis for modifying or designing other methods and systems for carrying out the same purposes of the present invention. Those skilled in the art should also realize that such equivalent assemblies do not depart from the spirit and scope of the invention in its broadest form.

Figure 1:
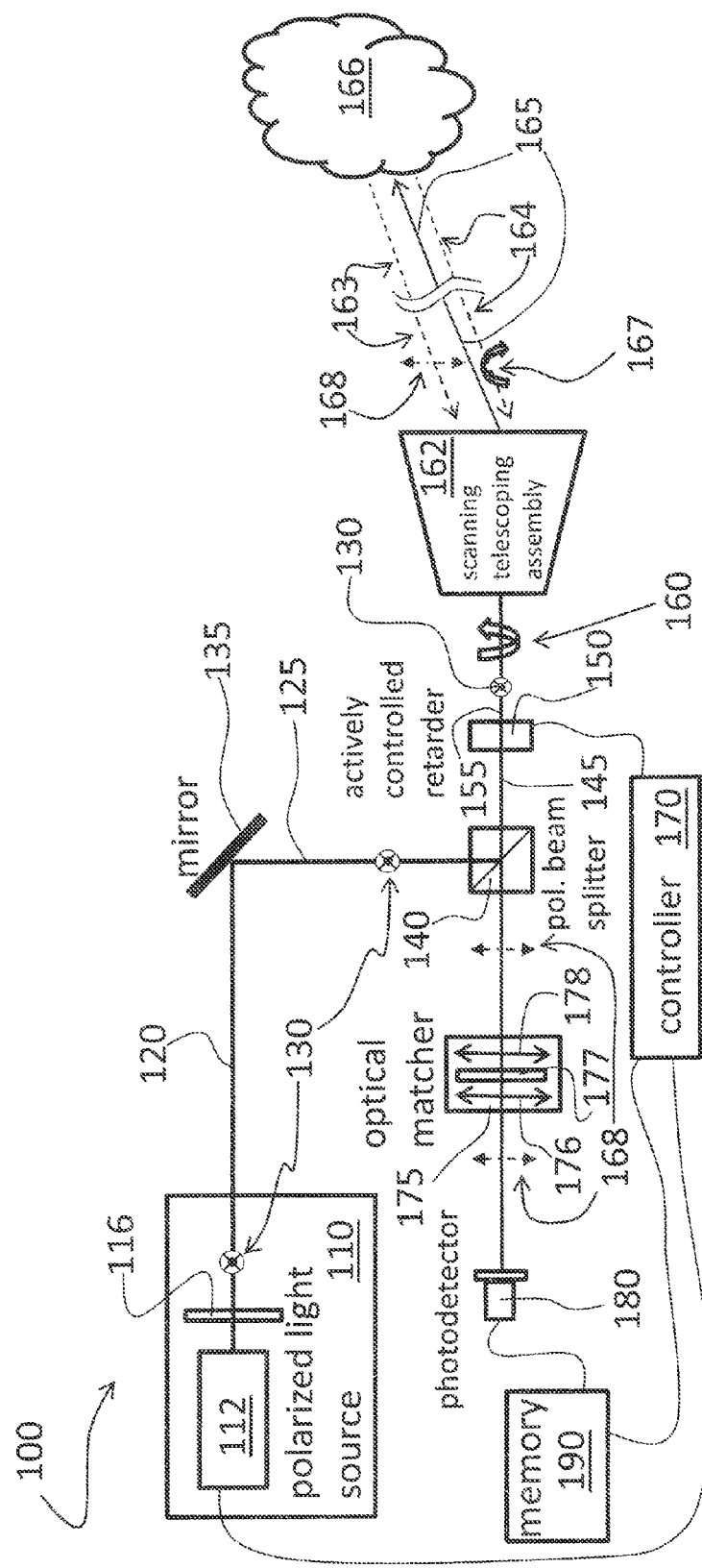
FIG. 1 is an illustration of an exemplary embodiment of the polarization switching lidar device according to the present invention.

One exemplary embodiment of the polarization switching lidar device 100 for remote detection and characterization of atmospheric aggregation of particulates in accordance with the present invention is represented schematically in FIG. 1. The exemplary polarization switching lidar device includes a source 110 of a polarized pulsed laser light beam 120 linearly polarized in a predetermined direction of polarization 130 (for the illustrated example in FIG. 1, having the direction of polarization 130 perpendicular to the plane of the FIG. 1). The source 110 of the polarized pulsed laser light beam 120 may include a laser head 112 and a polarizer 116 arranged and oriented to define with sufficient accuracy the predetermined direction of polarization 130. The laser head 112 of the illustrated embodiment incorporates commercial Photonics Industries International, Inc. Nd:YVO$_4$ laser head arranged to a pulse rate ranging from 1 kHz to 150 kHz. It should be noted that a plethora of commercial or experimental lasers including, but not limited to: laser diodes, fiber lasers, diode-pumped solid-state lasers, and lamp-pumped solid-state lasers, are known to the practitioners and may be arranged in various pulse modes of operation (some exhibiting pulse length shorter than 50 ns) and used in different embodiments of the present invention.

The embodiment illustrated in FIG. 1 utilizes a direction controlling mirror 135 arranged to reflect the polarized pulsed laser light beam 120 and to redirect the reflected polarized pulsed laser light beam 125 in the direction of a polarizing beam splitter 140 arranged to intersect the reflected polarized pulsed laser light beam 125 and to redirect a portion of the reflected polarized pulsed laser light beam 125 in the direction of an actively controlled retarder 150. More particularly, the polarizing beam splitter 140 of the illustrated embodiment is oriented such that the reflected polarized pulsed laser light beam 125 linearly polarized in predetermined direction of polarization 130 is redirected while any component of the light beam 125 exhibiting linear polarization substantially different from the predetermined direction of polarization 130 is effectively absorbed in the polarizing beam splitter 140 and/or associated supporting structures.

The actively controlled retarder 150 is arranged to intersect the redirected portion 145 of the reflected polarized pulsed laser light beam 125, and to be controllably alternated between a zero retardation state and a quarter-wave retardation state by application of an appropriate control signal customarily characterized by at least two distinct voltage levels.

In particular, an actively controlled retarder 150 of the illustrated embodiment may be implemented so that during a predetermined time period when the "lower level" voltage signal is applied to a control input pin, no significant phase retardation is added to the light traversing an active medium of the actively controlled retarder 150, while when the "high level" voltage signal is applied to the control input pin the actively controlled retarder 150 behaves essentially as a quarter-wave plate causing a quarter-wave ($\Delta\phi=\pi/2$) retardation of the phase of the appropriately polarized traversing the active medium of the actively controlled retarder 150. Consequently, for the example illustrated schematically in FIG. 1, when the active medium of the actively controlled retarder 150 is in the zero retardation state ($\Delta\phi=0$), the polarized pulsed laser light beam exiting the actively controlled retarder 150 is linearly polarized in the predetermined direction 130, while the transmitted portion 155 exiting the actively controlled retarder 150 of the polarized pulsed laser light beam 145 is circularly polarized in a predetermined rotational sense 160 when the actively controlled retarder 150 is in the quarter-wave retardation state and arranged to have an optical axis oriented at 45° relative to the predetermine direction of liner polarization 130.

Many actively controlled retarders 150 (such as ones based on Pockles cells technology) are known to change retardation states during time intervals in order of 1 ns (e.g. KD*P Pockels Cells available from Cleveland Crystals) and can be arranged to support pulse operations having pulse length shorter than 50 ns.

Therefore, in the exemplary embodiment illustrated in FIG. 1, the polarized pulsed laser light beam 145 is essentially polarized in the predetermine direction of liner polarization 130, such that the transmitted portion 155 of the polarized pulsed laser light beam 145 exiting the actively controlled retarder 150 remains linearly polarized in the predetermine direction of liner polarization 130 when the actively controlled retarder 150 is in zero retardation state, while the transmitted portion 155 of the polarized pulsed laser light beam 145 exiting the actively controlled retarder 150 becomes circularly polarized in a predetermined rotational sense 160 when the actively controlled retarder 150 is in the quarter-wave retardation state.

The exemplary embodiment of the polarization switching lidar device in FIG. 1 includes a directable telescoping assembly 162 arranged to intersect the transmitted portion 155 of the polarized pulsed laser light beam 145 exiting the actively controlled retarder 150 and to be controllably directable (i.e. to be manually or automatically specially oriented in a direction of interest in order to observe a predetermined sets of space angles) so as to redirect the intersected transmitted portion 155 of the polarized pulsed laser light beam 145 into the predetermined set of space angles of interest, while collecting portions 163 or 164 of depolarized backscattered photons from the scanned polarized pulse laser light beam 165 backscattered by the at least one airborne aggregation of particulates 166. The directable telescoping assembly 162 is also arranged to redirect the collected portions 163 or 164 of depolarized backscattered photons onto the actively controlled retarder 150 and further onto the polarizing the beam splitter 140.

The directable telescoping assembly 162 of the particular exemplary embodiment illustrated in FIG. 1 includes a scanning telescope incorporating an internal scanner positioned between the telescope principle optical elements is described in the co-pending co-owned U.S. patent application Ser. No. 12/547,237, entitled: TELESCOPE WITH A WIDE FIELD OF VIEW INTERNAL OPTICAL SCANNER, which is here incorporated by reference in its entirety. As disclosed in more details in the incorporated U.S. patent application Ser. No. 12/547,237, the directable telescope assembly 162 of the exemplary embodiment is based on a classic Maksutov-Cassegrain telescope reflector configuration (more particularly, Questar FR7 model commercially obtained for example from Company Seven Astro-Optics Division of Montpelier, Md., and modified by the Sigma Space Corporation to conform with the components of the disclosed polarization switching lidar device in accordance to standard optical engineering principles and practices.) It may be noted that other telescope systems including for example Galilean, Keplerian, Newtonian, Cassegrain, Maksutov-Cassegrain, Argunov-Cassegrain, Ritchey-Chratien, Dall-Kirkham, Gregorian, Hershelian, Schiefspiegler, and Yolo, telescope configuration or any combination of the listed telescope configurations may be integrated and used in various embodiments of the present invention.

In addition, it may be discerned that different scanning telescope devices incorporating a telescope and an external scanner may be used in other embodiments of the polarization switching lidar device in accordance with the present invention. For example, a scanning telescope device having an external scanner is disclosed in more details in the co-pending and co-owned U.S. patent application Ser. No. 11/683,549, entitled: SCANNER/OPTICAL SYSTEM FOR THREE-DIMENSIONAL LIDAR IMAGING AND POLARIMETRY, here also incorporated by reference in its entirety.

It may be also noted that propagation of the scanned polarized pulse laser light beam 165 through the atmosphere containing negligible amount of scatterers results in substantially no backscattered photons and no significant depolarization of the scanned polarized pulse laser light beam 165 which remains either linearly polarized in the predetermined direction of polarization 130 or in the predetermined rotational sense 160, as disclosed above. In contrast, when the scanned polarized pulse laser light beam 165 intersects at least one airborne aggregation of particulates 166, the resulting interaction may increase probabilities of backscatter. More particularly, it is known that when the airborne aggregation of particulates 166 includes a significant concentrations of symmetric constituents (like droplets of water or other liquids like acid or salts solutions or suspensions) elastic backscattering processes may predominate resulting in a geometric inversion of the circular polarization of the backscattered photons from the predetermined rotational sense 160 of circular polarization into a circular polarization having an opposite rotational sense 167 relative to the predetermined rotational sense 160. Conversely, when the airborne aggregation of particulates 166 includes a significant concentrations of irregularly shaped solid particulates (like ice crystals or particulates of sooth, smoke, industrially or naturally generated dust particulates, solid particulates incorporating carbon, solid particulates incorporating salt, mixtures and combinations of above particulates etc.) the backscattering may result in an enhanced depolarization of the scanned polarized pulse laser light beam 165 from the linearly polarized in the predetermined direction of polarization 130 into a linearly polarized in the direction of polarization 168 which is perpendicular to the predetermined direction of polarization 130.

Consequently, as the actively controlled retarder 150 of polarization switching lidar device of the present invention rapidly alternates between the zero retardation state $\Delta\phi=0$ and the quarter-wave retardation state $\Delta\phi=\pi/2$ (as controlled by a preprogrammed controller 170) causing alternations of polarization states of collected backscattered photons between the linearly polarized state 168 and circularly polarized state 167. As the directable telescoping assembly 162 redirects the collected portions 163 or 164 of depolarized backscattered photons onto the actively controlled retarder 150 and further onto the polarizing the beam splitter 140, the collected portion 164 traverses the actively controlled retarder 162 as being in the quarter-wave retardation state, while the collected portion 163 traverses the actively controlled retarder 162 as being in the zero retardation state. Therefore, the polarization states of both collected portions 163 and 164 of interest are arranged to be in the state of the linearly polarized in the direction of polarization 168 which is perpendicular to the predetermined direction of polarization 130, and thus arranged to traverse the polarization beam splitter 140 with minimal loss. In opposition, a significant portion of undesirable "stray light", diffusively reflected or scattered by impurities and imperfections of the constituent parts of the polarization switching lidar device, remain polarized predominantly in the predetermined direction of polarization 130 and, ipso facto, filtered out by the polarization beam splitter 140.

The exemplary embodiment illustrated in FIG. 1 features an optical matcher 175 arranged to collect a fraction of the transmitted portion 155 of backscattered photons exiting the polarizing beam splitter and focus the collected fraction of depolarized backscattered photons onto a photodetector 180 arranged to generate at least one electronic signal proportional to the collected portion of depolarized backscattered photons. The optical matcher 175 of the illustrated exemplary embodiment is based on a narrowband filter 177 arranged to narrowly transmit photons of selected wavelength (such is the narrowband filter having central wavelength at 532,07 nm and FWHM no greater than 0.15 nm, available as a custom product from Barr Associates, Inc. of Westford, Mass.) The incoming photons may be collimated using an collimating lens 178 (e.g. Plano-Convex Lens 6.0 mm Dia.×9.0 mm focal length commercially available from Edmund Optics of Barrington, N.J.) to ensure narrowband performance of the narrowband filter 177, while an additional lens 176 (e.g. Mounted Geltech Aspheric Lens, AR-Coated: 350-700 nm, part number C230TME-A, from Thorlabs of Newton, N.J.) may be used to match the filtered photons to the photodetector 180 (e.g. Single Photon Counting Module SPCM-AQR-14-FC commercially available from PerkinElmer's Marketing and Marketing Communications of Salem, Mass.)

The photodetector 180 is arranged to generate at least one electronic signal proportional to the collected portion of depolarized backscattered photons which can be digitized and stored into a dedicated memory 190. In the embodiment represented in FIG. 1 the memory 190 is controlled by the controller 170 so as to generate at least two separate digital records of which at least one is generated and stored during the time period when the actively controlled retarder 150 is in the zero retardation state ($\Delta\phi=0$) and at least another digital record is generated and stored during the quarter-wave retardation state ($\Delta\phi=\pi/2$) of the actively controlled retarder 150 (as controlled by a preprogrammed controller 170). Therefore, at least one digital record may be predominantly sensitive to the backscattering from the aggregations irregularly shaped particulates (when $\Delta\phi=0$), while at least another digital record may be predominantly sensitive to the backscattering on the aggregations of predominantly symmetric particulates (when $\Delta\phi=\pi/2$). Thus, the polarization switching lidar embodiment illustrated in FIG. 1 may exhibit a fundamental simplicity of a "single beam" ("single channel") scattering device, while the resulting digital records may enjoy enhanced sensitivities usually associated with significantly more complex multi-beam ("multichannel") lidar devices.

In a framework of a more concise theoretical consideration of the lidar measuring sequence as described in the above recitation, a lidar backscattered signal can be considered to be essentially incoherent and may be represented sufficiently accurately as a 4-component Stokes vector and analyzed using Mueller matrix calculus. Therefore, the lidar measurement sequence may be symbolically represented as a sequence of Mueller operators acting on a initial polarization vector $\vec{P}_S$ as:

$$\vec{P}_{final} = M_{LPH} M_{LCR}(\phi,-45) M_{atm} M_{LCR}(\phi,+45) M_{LPV} \vec{P}_S \quad (Eq. 1)$$

where $M_{LPV}$ stands for the PBS acting as a linear polarizer with axis aligned to the vertical, $M_{LCR}(\phi,+45)$ stands for the actively controlled retarder with retardation $\phi$ aligned with fast axis at +45° to vertical, $M_{atm}$ represents the interaction with the atmosphere, $M_{LCR}(\phi,-45)$ is again the actively controlled retarder but now with fast axis aligned at −45° to vertical, and $M_{LPH}$ is the PBS now acting as a linear polarizer with axis aligned horizontally. Note that the angles are defined as positive clockwise while facing in the direction of propagation. When the direction of propagation is reversed for the returning light, the angles are also reversed. Mueller matrices do not represent optical components so much as optical interactions explaining why different Mueller matrices are used to represent the same optical component. With the exception of $M_{atm}$, the other operators represent the actions of elementary optical elements with known form.

The Mueller matrix for the atmosphere is, as well understood in standard practice, a changing quantity and is a subject of intense study [9-10]. For a common simple case of single scattering on particles having a plane of symmetry or random orientation (which includes spheres, randomly oriented ice crystals, and horizontal plates) we benefit from substantial cancellation of matrix elements based on symmetry arguments to obtain $$M_{atm} = a \begin{bmatrix} 1 & 0 & 0 & 0 \\ 0 & 1-d & 0 & 0 \\ 0 & 0 & d-1 & 0 \\ 0 & 0 & 0 & 2d-1 \end{bmatrix}, \quad (Eq. 2)$$

where a is proportional to the magnitude of the return signal and d is indicative of the degree to which the return signal is depolarized. For d=0, $M_{atm}$ is identical to Mueller matrix for normal incidence on a perfect mirror.

Starting with $\vec{P}_S$ taken as linearly polarized vertically, the equation Eq. 1 together with the equation Eq. 2 yields final polarization vectors $\vec{P}_\perp$, $\vec{P}_\square$, $\vec{P}_{RH}$, and $\vec{P}_{LH}$ as $$\vec{P}_\perp = \begin{pmatrix} d/2 \\ d/2 \\ 0 \\ 0 \end{pmatrix}, \vec{P}_\square = \begin{pmatrix} 1-d/2 \\ 1-d/2 \\ 0 \\ 0 \end{pmatrix}, \quad (Eq. 3)$$

$$\vec{P}_{RH} = \begin{pmatrix} 1-d \\ d-1 \\ 0 \\ 0 \end{pmatrix}, \vec{P}_{LH} = \begin{pmatrix} d \\ -d \\ 0 \\ 0 \end{pmatrix}$$

Several relevant depolarization ratios can be defined as:

$$\delta_{linear} = \frac{\vec{P}_\perp(1)}{\vec{P}_\square(1)}, \delta_{circ} = \frac{\vec{P}_{LH}(1)}{\vec{P}_{RH}(1)}, \text{ and } \delta_{MPL} = \frac{\vec{P}_\perp(1)}{\vec{P}_{RH}(1)}. \quad (Eq. 4)$$

Combining Eq. 3 and Eq. 4 results in:

$$\delta_{linear} = \frac{d}{2-d}, \delta_{circ} = \frac{d}{1-d}, \text{ and } \delta_{MPL} = \frac{d}{2(1-d)}. \quad (Eq. 5)$$

Equation Eq. 5 in combination with Eq. 3 leads to following relationships:

$$\delta_{linear} = \frac{\delta_{MPL}}{\delta_{MPL}+1} \text{ and } \delta_{circ} = 2 \times \delta_{MPL}, \quad (Eq. 6)$$

$$\text{or } \delta_{MPL} = \delta_{circ}/2 = \delta_{linear}/(1-\delta_{linear}),$$

which can be interpreted as consequences of lidar signal power conservation, as may be expected.

Figure 2:
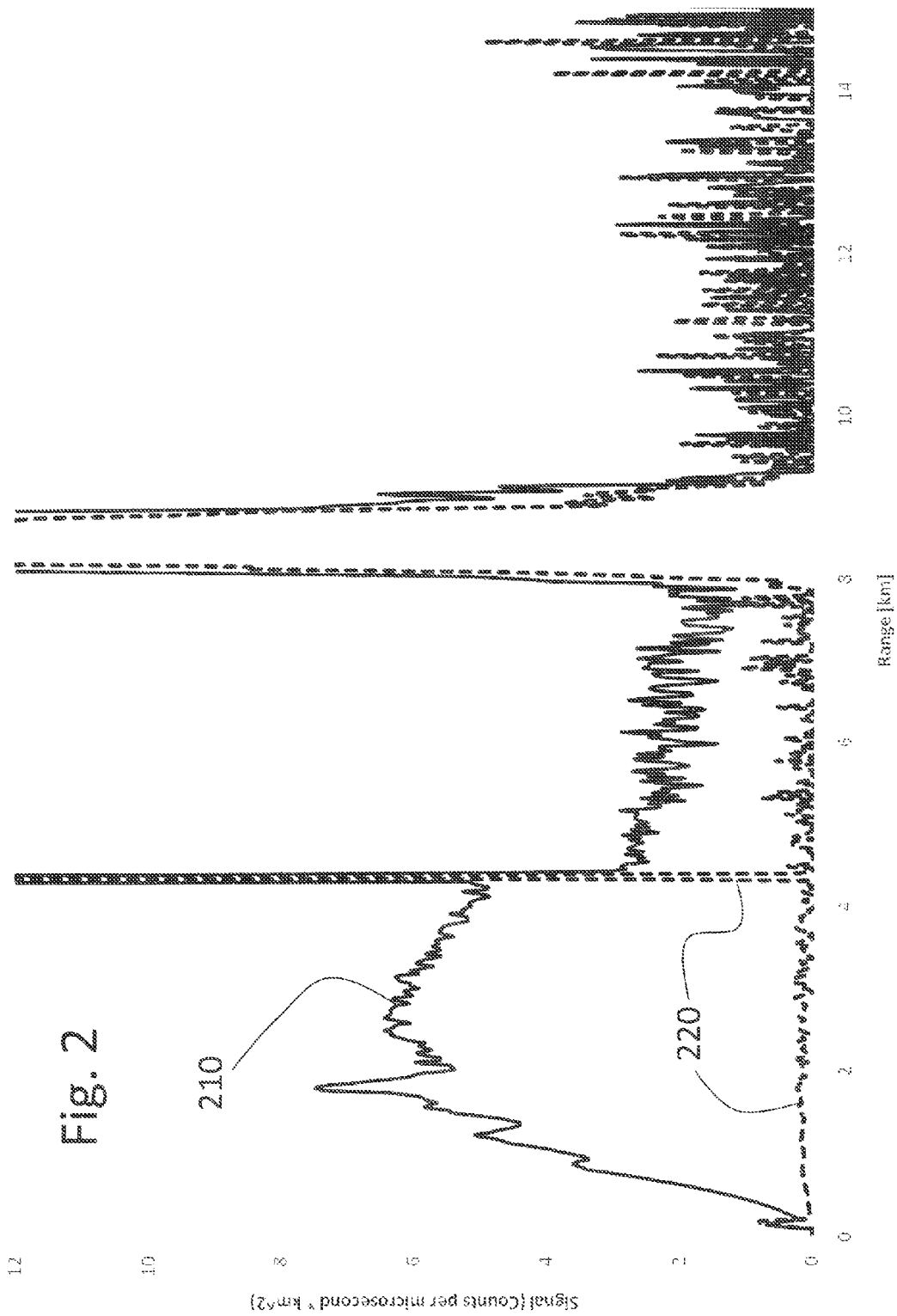
FIG. 2 is an illustration of an exemplary measurement results from an embodiment of the polarization switching lidar device according to the present invention.

One example of the results of measurements of the $\vec{P}_\perp(\Delta\phi=\pi/2)$ and the $\vec{P}_\perp(\Delta\phi=0)$ signals versus range obtained from the exemplary embodiment of FIG. 1 is illustrated in FIG. 2. On the horizontal axis range up to 15 km is shown. The vertical axis shows range-square corrected signals, i.e. (total backscatter signal−background signal)* range$^2$. The units of the range-square corrected signal are counts/microsecond*km$^2$. The solid trace 210 indicates the range-square corrected signal resulting predominantly from the backscattering on the airborne aggregation 166 of symmetric particulates corresponding to the $\vec{P}_\perp(\Delta\phi=\pi/2)$, while the dashed trace 220 indicates the range-square corrected signal resulting predominantly from the backscattering on the airborne aggregation 166 of particulates generally lacking the spherical symmetry corresponding to the $\vec{P}_\perp(\Delta\phi=0)$ signal.

The particular measurements yielding results illustrated in FIG. 2 are made for 60 seconds with the retardation state of the actively controlled retarder alternating between the zero and the quarter-wave retardation states. The range-square corrected signals 210 and 220 are accumulated in separate locations in the memory 190. The laser 112 of this exemplary embodiment has a pulse repetition rate of 2500 Hz. Effectively, 30 seconds or backscattered signals from 75,000 laser pulses are integrated in each range-square corrected signal and displayed. Typical pulse energy for this type of measurements is 6 microjoules. The range resolution of 30 m is estimated.

As is seen in the range-square corrected signal 210 given in a solid trace, a large backscatter is obtained from the primarily spherical aggregates present in the lower atmosphere. The $\vec{P}_\perp(\Delta\phi=0)$ backscatter, proportional to the dashed trace 220, remains low at these ranges. At the 4.5 and 8 km ranges, two cloud layers may be observed in both signals 210 and 220. The backscatter from clouds is a strong because of a relative increase of density of the scatterers, and exhibits depolarization that is observed as the $\vec{P}_\perp(\Delta\phi=0)$ backscatter due to the presence of non-spherical ice crystals present in these clouds.

The signals 210 and 220 in the 0-2 km range exhibit increases with distance before reaching a peak and subsequently falling off with range. This may be related to an instrument function of geometric overlap, known to be a characteristic of many lidars. The instrument overlap function normally corresponds to the design features of the particular telescopes including size, axis-to-axis distance between transmitter and receiver telescopes (in cases of lidars having separate transmitter and receiver units), the field of view the telescoping assembly designs, etc.

Figure 3:
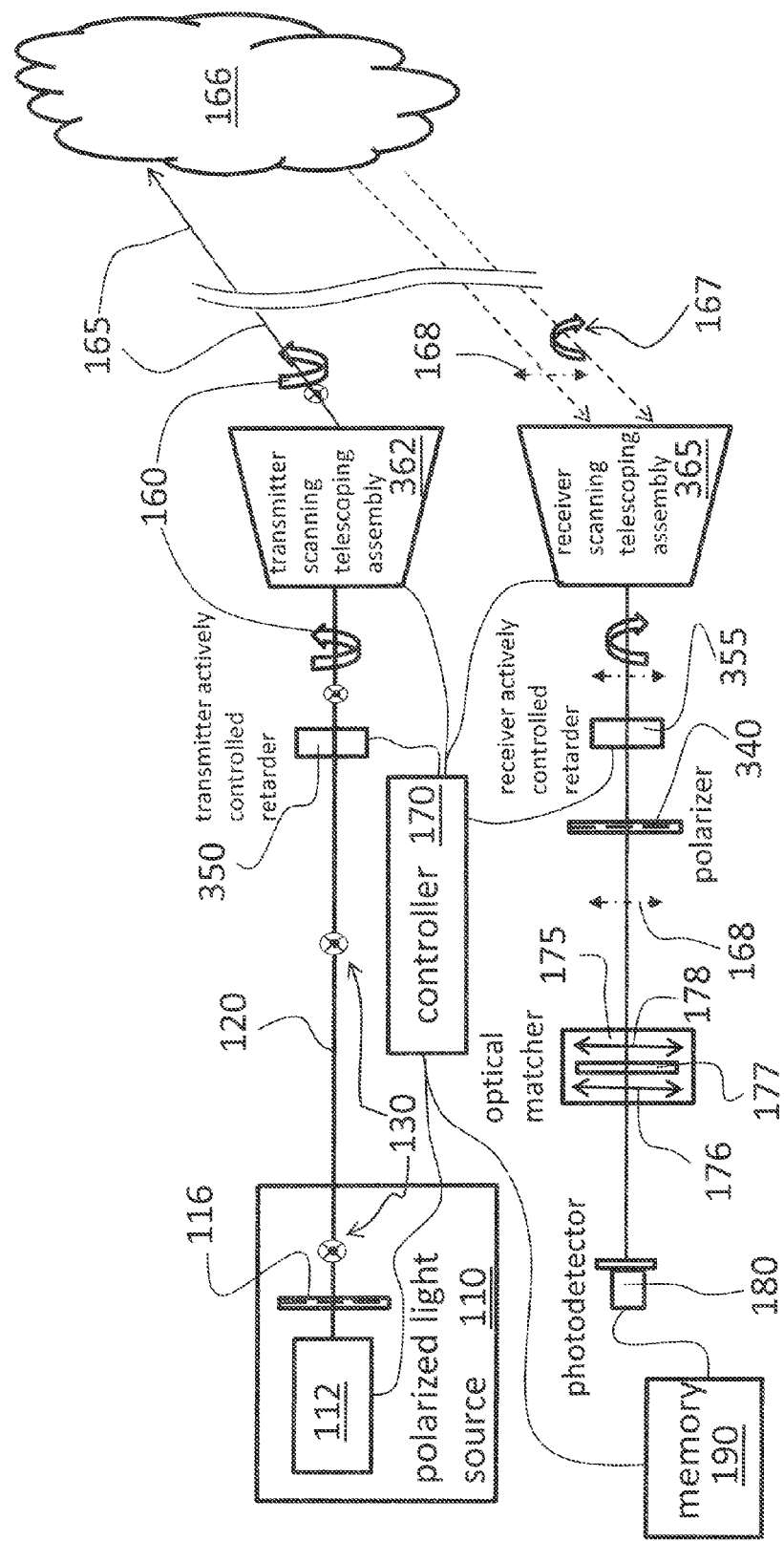
FIG. 3 is an illustration of a different exemplary embodiment of the polarization switching lidar device according to the present invention.

An exemplary embodiment of a polarization switching lidar device having aforementioned separate transmitter and receiver telescope assemblies is shown schematically in FIG. 3. The exemplary embodiments in FIG. 1 and FIG. 3 share several parts arranged to performing corresponding operations as described above regarding FIG. 1. Those shared parts are indicated in FIG. 3 using same corresponding reference numerals as introduced in FIG. 1. For example, the controller 170 in FIG. 3 is arranged to simultaneously control and synchronize a transmitter actively controlled retarder 350 and a receiver actively controlled retarder 355 both having the arrangement and the functions analogues to those of the actively controlled retarder 150. Similarly, the controller 170 is arranged to control the transmitting directable telescoping assembly 362 and the transmitting directable telescoping assembly 365 to have essentially overlapping fields of view in order to obtain backscattering signals from predetermined volumes of the airborne aggregation of particulates 166.

One notable difference between embodiments in FIGS. 1 and 3 is the replacement of the polarization beam splitter 140 with an additional polarizer 340. As the function of combining/separating of the optical paths of transmitted and received laser beams performed by the polarization beam splitter 140 is, by definition, absent from the embodiment having separated transmitted and received beam paths in FIG. 3, a simpler polarizer 340, generally similar to the polarizer 116 but rotated by $\pi/2$ (relative to the polarizer 116) may be sufficient for suppression of the "stray light" discussed above regarding FIG. 1.

Figure 4:
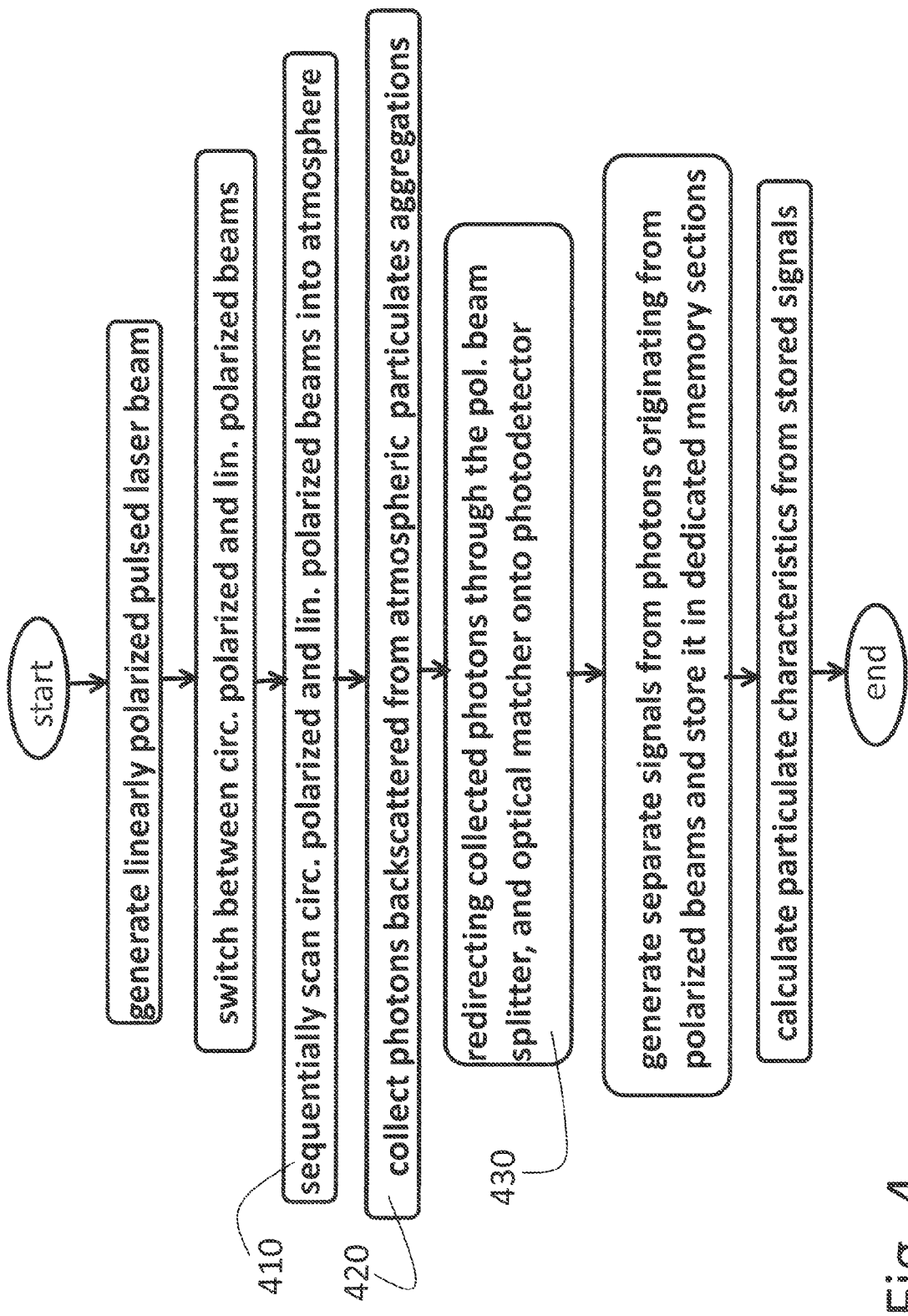
FIG. 4 is an illustration of a flow chart diagram of operation of an exemplary embodiment of the polarization switching lidar device according to the present invention.

A method for remote detection and characterization of at least one airborne aggregation of particulates utilizing a polarization switching lidar device of the present invention is generally related to the arrangements of the disclosed embodiments schematically given in FIGS. 1 and 3. More particularly, the principle steps of the method are given in the flowchart in FIG. 4, which closely corresponds to the exemplary embodiment in FIG. 1. The method corresponding to the embodiment in FIG. 3, generally differs only in details from the flowchart in FIG. 4. For example, the steps 410 and 420 encompasses transmitting/receiving functions using the single directable telescoping assembly 162 and using the transmitting directable telescoping assembly 362 and the receiving directable telescoping assembly 365, but the step 430 generally pertains to the embodiment illustrated in FIG. 1 as the embodiment illustrated in FIG. 3 may include the polarizer 340 instead of the polarization beam splitter 140.

Several embodiments of applications of the polarization switching lidar device 100 are illustrated in FIG. 5. For example, the lidar device 100 may be arranged on an flying vehicle 510 and having field of view 520 arranged to detect clouds 566 and/or atmospheric aggregations of particulates 166 at altitudes equal or below the flight altitude (including the height $h_v$ relative to a predetermined reference level 570 and the absolute altitude of the reference surface 570) of the (over) flying vehicle 510.

In another embodiment illustrated in FIG. 5, the polarization switching lidar device 100 is arranged on a surface 530 erected on a stationary or semi-stationary (transportable) structure having altitude h relative to the reference surface 570. Such an installation can accommodate the field of view 520 which may include clouds 566 at altitudes above the altitude of the surface 530 or low-altitude particulate aggregations 556 characteristic of altitudes below the average altitude of the surface 530. In addition, such an embodiment can be arranged to detect time-dependent characteristics of the aggregations 166, 556, and/or 566 allowing for positive identification of sources 580 of the particulates of interest and determination of habitudes of the characterized sources 580.

The present invention has been described with references to the exemplary embodiments arranged for different applications. While specific values, relationships, materials and components have been set forth for purposes of describing concepts of the invention, it will be appreciated by persons skilled in the art that numerous variations and/or modifications may be made to the invention as shown in the specific embodiments without departing from the spirit or scope of the basic concepts and operating principles of the invention as broadly described. It should be recognized that, in the light of the above teachings, those skilled in the art can modify those specifics without departing from the invention taught herein. Having now fully set forth the preferred embodiments and certain modifications of the concept underlying the present invention, various other embodiments as well as certain variations and modifications of the embodiments herein shown and described will obviously occur to those skilled in the art upon becoming familiar with such underlying concept. It is intended to include all such modifications, alternatives and other embodiments insofar as they come within the scope of the appended claims or equivalents thereof. It should be understood, therefore, that the invention may be practiced otherwise than as specifically set forth herein. Consequently, the present embodiments are to be considered in all respects as illustrative and not restrictive.

We claim:

1. A polarization switching lidar device for remote detection and characterization of at least one airborne aggregation of particulates comprising:
    a source of a polarized pulsed laser light beam;
    a direction controlling mirror arranged to reflect the polarized pulsed laser light beam and redirect the reflected polarized pulsed laser light beam;
    a polarizing beam splitter arranged to intersect the reflected polarized pulsed laser light beam and to redirect a portion of the reflected polarized pulsed laser light beam;
    an actively controlled retarder arranged to intersect the redirected portion of the reflected polarized pulsed laser light beam, and to be controllably alternated between a zero retardation state and a quarter-wave retardation state such that the transmitted portion of the polarized pulsed laser light beam exiting the actively controlled retarder is linearly polarized in a predetermined direction when the actively controlled retarder is in the zero retardation state, while the transmitted portion of the polarized pulsed laser light beam exiting the actively controlled retarder is circularly polarized in a predetermined rotational sense when the actively controlled retarder is in the quarter-wave retardation state;
    a directable telescoping assembly arranged to intersect the transmitted portion of the polarized pulsed laser light beam exiting the actively controlled retarder and to controllably redirect the intersected polarized pulsed laser light beam into a predetermined space angle while collecting at least a portion of depolarized backscattered photons from the scanned polarized pulse laser light beam backscattered by the at least one airborne aggregations of particulates, and to redirect the collected portion of depolarized backscattered photons onto the polarizing beam splitter;
    an optical matcher arranged to collect a fraction of backscattered photons exiting the polarizing beam splitter and focus the collected fraction of depolarized backscattered photons onto a photodetector arranged to generate at least one electronic signal proportional to the collected portion of depolarized backscattered photons.

2. The polarization switching lidar device of claim 1, wherein the source of the polarized pulsed laser light beam includes a laser head and a half-wave plate.

3. The polarization switching lidar device of claim 2, wherein the laser head incorporates a laser chosen from a set of lasers consisting of laser diodes, fiber lasers, diode-pumped solid-state lasers, and lamp-pumped solid-state lasers.

4. The polarization switching lidar device of claim 2, wherein the half-wave plate is arranged to adjust a linear polarization of the polarized pulsed laser light beam emitted by the laser head.

5. The polarization switching lidar device of claim 1, wherein the polarizing beam splitter is rotationally oriented to optimally redirect the portion of the reflected polarized pulsed laser light beam.

6. The polarization switching lidar device of claim 5, wherein the polarizing beam splitter is chosen from the set of polarizing beam splitters consisting of thin film plate polarizing beam splitter, holographic polarizing beam splitter, polarizing beam splitter cube, Nicol prism, Wollaston prism, Glan-Thomson prism, Glan-Taylor prism, Glan-Foucault prism, Sénarmont prism, and Rochon prism.

7. The polarization switching lidar device of claim 1, wherein the actively controlled retarder is a voltage-controlled retarder chosen from a set consisting of liquid crystal retarders, voltage-controlled wave plates, and Pockels cells.

8. The polarization switching lidar device of claim 1, wherein the actively controlled retarder exhibits a transition time between the zero retardation state and the quarter-wave retardation state between 5 μs and 100 μs.

9. The polarization switching lidar device of claim 1, wherein the actively controlled retarder exhibits a transition time between the zero retardation state and the quarter-wave retardation state does not exceed 50 ns.

10. The polarization switching lidar device of claim 1, wherein the directable telescoping assembly incorporates an internal scanning device arranged between principal optical elements of a scanning telescope.

11. The polarization switching lidar device of claim 1, wherein the directable telescoping assembly incorporates an external scanning device arranged outside of an optical path between principal optical elements of a scanning telescope.

12. The polarization switching lidar device of claim 1, wherein the sirectable telescoping assembly incorporates a telescope arranged in a telescope configuration chosen from a group of telescope configurations consisting of Galilean, Keplerian, Newtonian, Cassegrain, Maksutov-Cassegrain, Argunov-Cassegrain, Ritchey-Chratien, Dall-Kirkham, Gregorian, Hershelian, Schiefspiegler, Yolo, and any combination of the listed telescope configurations.

13. The polarization switching lidar device of claim 1, wherein the optical matcher includes a narrow band pass filter and at least one lens.

14. The polarization switching lidar device of claim 1, wherein the photodetector is arranged to generate at least one time-dependent analog electronic signal proportional to the collected fraction of depolarized backscattered photons and to digitize the least one time-dependent analog electronic signal into at least one time-dependent digital signal stored in a memory unit.

15. The polarization switching lidar device of claim 14, including a control unit arranged to control timing of alternations of the actively controlled retarder between the zero retardation state and the quarter-wave retardation state and to synchronize the memory unit arranged sequentially store at least two separate sequences of the at least one time-dependent digital signal so that wherein one of the at least two separate sequences detected during the zero retardation state is stored in at least one segment of the memory unit, while another of the at least two sequences of the at least one time-dependent digital signal detected during the quarter-wave retardation state is stored in at least another segment of the memory unit.

16. The polarization switching lidar device for remote detection and characterization of an airborne aggregations of particulates of claim 1, wherein the polarization switching lidar device is arranged in at least semi-stationary position on an observation surface having an average observation surface altitude and arranged to detect and characterize the airborne aggregations of particulates having an average altitude greater than the average observation surface altitude.

17. The polarization switching lidar device for remote detection and characterization of an airborne aggregations of particulates device of claim 1, wherein the polarization switching lidar device is arranged in at least semi-stationary position on an observation surface having an average observation surface altitude and arranged to detect and characterize the airborne aggregations of particulates having an average altitude smaller than or equal to the average observation surface altitude.

18. The polarization switching lidar device of claim 16, wherein the airborne aggregations of particulates include particulates in at least one cloud at an altitude greater than the average altitude of the observation surface.

19. The polarization switching lidar device of claim 18, wherein the particulates in the at least one cloud include particulates from the set of particulates consisting of water droplets, ice crystals, droplets of acidic solutions, solid particulates incorporating carbon, solid particulates incorporating soil dust, and mixtures and combinations of listed particulates.

20. The polarization switching lidar device for remote detection and characterization of an airborne aggregations of particulates device of claim 1, wherein the polarization switching lidar device is arranged on a flying vehicle, flying at an predetermined altitude, and the polarization switching lidar device is directed substantially downward so as to detect and characterize the airborne aggregations of particulates in the atmosphere at variable altitudes lower than the predetermined altitude of the flying vehicle.

21. The polarization switching lidar device of claim 16, wherein the characterization of at least one airborne aggregation of particulates includes at least a position determination of a source of the at least one airborne aggregation of particulates based on changes in the at least one electronic signal proportional to the collected fraction of depolarized backscattered photons.

22. The polarization switching lidar device of claim 18, wherein the characterization of at least one airborne aggregation of particulates includes determination of at least a position and a probable habitude of a source of the at least one airborne aggregation of particulates based on changes in the at least one electronic signal proportional to the collected fraction of depolarized backscattered photons.

23. A method for remote detection and characterization of at least one airborne aggregation of particulates utilizing a polarization switching lidar device, the method comprising:
generating a linearly polarized pulsed laser light beam having a predetermined direction of linear polarization;
using at least one the actively controlled retarder, sequentially controllably switching a polarization state of the polarized pulsed laser light beam between a circularly polarized state polarized into a predetermined rotational sense, when the at least one actively controlled retarder is controllably switched into a quarter-wave retardation state, and into a linearly polarized state linearly polarized in a direction substantially equivalent to the predefined direction of linear polarization when the at least one actively controlled retarder is controllably switched into a zero retardation state such that a transmitted portion of polarized pulsed laser light beam exiting the at least one actively controlled retarder is linearly polarized in the predetermined polarization direction when the at least one actively controlled retarder is in the zero retardation state while the transmitted portion of polarized pulsed laser light beam exiting the at least one actively controlled retarder is circularly polarized having the predetermined rotational sense when the at least one actively controlled retarder is in the quarter-wave retardation state;

scanning the transmitted portion of polarized pulsed laser light beam exiting the actively controlled retarder by at least one telescoping assembly arranged to intersect the transmitted portion of polarized pulsed laser light beam exiting the actively controlled retarder and controllably redirect the intersected polarized pulsed laser light beam into a predetermined space angle toward at least one airborne aggregation of particulates;

backscattering the scanned transmitted portion of the polarized pulsed laser light beam sequentially polarized into the circularly polarized state having the predetermined rotational sense and into the linearly polarized state having the predetermined polarization direction so that a fraction of photons scatters back from at least one airborne aggregation of particulates such that the photons in circularly polarized state having the predetermined rotational sense acquire an opposite rotational sense of circular polarization, while at least a fraction of photons polarized in the predetermined linearly polarized state, when scattered back, acquires a linear polarization state polarized in an orthogonal direction relative to the predetermined direction of linear polarization;

collecting photons from the predetermined space angle and redirecting the collected photons onto the actively controlled retarder by the at least one telescoping assembly;

sequentially converting by the actively controlled retarder in the quarter-wave retardation state the collected backscattered photons having the circularly polarized state polarized in the opposite rotational sense relative to the rotational sense of the predetermined sense of circular polarization into the linearly polarized state having the polarization state polarized in an orthogonal direction relative to the predetermined direction of linear polarization, while transmitting the scattered back photons polarized in the linear polarization state having orthogonal direction of linear polarization relative to the predetermined direction of linear polarization when the actively controlled retarder in the zero retardation state, and redirecting the converted photons onto the polarizing beam splitter;

selectively separating the converted photons collected sequentially onto the polarizing beam splitter by transmitting only the linearly polarized photons having orthogonal direction of linear polarization relative to the predetermined direction of linear polarization;

optically matching the transmitted linearly polarized photons having orthogonal direction of linear polarization relative to the predetermined direction of linear polarization using an optical matcher arranged to collect at least a fraction of the transmitted linearly polarized photons having orthogonal direction of linear polarization relative to the predetermined direction of linear polarization and focus the transmitted linearly polarized photons having orthogonal direction of linear polarization relative to the predetermined direction of linear polarization onto a photodetector arranged to generate at least two electronic signals proportional to the transmitted linearly polarized photons having orthogonal direction of linear polarization relative to the predetermined direction of linear polarization;

separating at least one electrical signal of the at least two electrical signals, the separated at least one electrical signal being generated during the quarter-wave retardation state, from the at least another electrical signal, the at least another electrical signal being generated during the zero retardation state of the actively controlled retarder, and storing the separated signals into at least two dedicated memory sections.

24. The method for remote detection and characterization of at least one airborne aggregation of particulates of claim 23, including a step of redirecting a transmitted portion of the linearly polarized pulsed laser light beam by a polarizing beam splitter arranged to intersect the linearly polarized pulsed laser light beam.

25. The method for remote detection and characterization of at least one airborne aggregation of particulates of claim 23, wherein the polarization switching lidar device is arranged in at least semi-stationary position on an observation surface having an average altitude and directed substantially upward so as to detect and characterize the airborne aggregations of particulates.

26. The method for remote detection and characterization of at least one airborne aggregation of particulates of claim 23, wherein the airborne aggregations of particulates include particulates in at least one cloud at an altitude greater than the average altitude of the observation surface.

27. The method for remote detection and characterization of at least one airborne aggregation of particulates of claim 25, wherein the particulates in the at least one cloud include particulates from the set of particulates consisting of water droplets, ice crystals, droplets of acidic solutions, solid particulates incorporating carbon, solid particulates incorporating soil dust, and mixtures and combinations of listed particulates.

28. The method for remote detection and characterization of at least one airborne aggregation of particulates of claim 23, wherein the polarization switching lidar device is arranged on a flying vehicle, flying at a predetermined altitude, and the polarization switching lidar device is directed substantially downward so as to detect and characterize the airborne aggregations of particulates in the atmosphere at variable altitudes lower than the predetermined altitude of the flying vehicle.

29. The method for remote detection and characterization of at least one airborne aggregation of particulates of claim 23, wherein the characterization of at least one airborne aggregation of particulates includes at least a position determination of a source of the at least one airborne aggregation of particulates based on changes in the at least one electronic signal proportional to the collected fraction of depolarized backscattered photons.

30. The method for remote detection and characterization of at least one airborne aggregation of particulates of claim 23, wherein the characterization of at least one airborne aggregation of particulates includes determination of at least a position and a probable habitude of a source of at least one airborne aggregation of particulates based on changes in the at least one electronic signal proportional to the collected fraction of depolarized backscattered photons.

* * * * *